United States Patent
Ottosen

(10) Patent No.: US 6,566,554 B1
(45) Date of Patent: May 20, 2003

(54) AMINOBENZOPHENONES AS INHIBITORS OF IL-1β AND TNF-α

(75) Inventor: Erik Rytter Ottosen, Ølstykke (DK)

(73) Assignee: Leo Pharmaceutical Products Ltd. a/s (Lovens Kemiske Fabrik Produktionsaktieselskab), Ballerup (DK)

( * ) Notice: Subject to any disclaimer, the term of this patent is extended or adjusted under 35 U.S.C. 154(b) by 0 days.

(21) Appl. No.: 10/031,075

(22) PCT Filed: Jul. 11, 2000

(86) PCT No.: PCT/DK00/00385
§ 371 (c)(1),
(2), (4) Date: Feb. 22, 2002

(87) PCT Pub. No.: WO01/05746
PCT Pub. Date: Jan. 25, 2001

Related U.S. Application Data

(60) Provisional application No. 60/144,166, filed on Jul. 16, 1999.

(51) Int. Cl.$^7$ .................. C07C 233/05; A61K 31/16
(52) U.S. Cl. ............ 564/211; 564/50; 564/74; 564/214; 564/328; 562/441; 560/27; 560/34; 560/43; 560/45; 554/36; 514/488; 514/534; 514/535; 514/538; 514/539; 514/563; 514/597; 514/599; 514/628; 514/648
(58) Field of Search ............. 560/27, 34, 43, 560/45; 562/441; 564/211, 50, 214, 328, 74; 554/36; 514/488, 534, 535, 538, 539, 563, 599, 597, 628, 648

(56) References Cited

U.S. PATENT DOCUMENTS 6,313,174 B1 * 11/2001 Otteson et al. ............. 514/616

FOREIGN PATENT DOCUMENTS

WO    WO 98/32730    7/1998

\* cited by examiner

Primary Examiner—Shailendra Kumar
(74) Attorney, Agent, or Firm—Birch Stewart Kolasch & Birch LLP

(57) ABSTRACT

The present invention relates to a compound of general formula (I) wherein $R_1$, $R_2$, and $R_3$ represents one or more, same or different substituents selected from the group consisting of halogen, hydroxy, mercapto, trifluoromethyl, amino, ($C_1$–$C_3$)alkyl, ($C_2$–$C_3$)olefinic group, ($C_1$–$C_3$) alkoxy, ($C_1$–$C_3$)akylthio, ($C_1$–$C_6$)alkylamino, ($C_1$–$C_3$) alkoxycarbonyl, cyano, —$CONH_2$, phenyl, or nitro; further $R_2$ can be hydrogen, and $R_3$ can be carboxy and carbamoyl; $R_4$ represents hydrogen, ($C_1$–$C_3$)alkyl, or allyl; X represents oxygen or sulphur; Q represents —(CO)—, —(CS)—, or a bond; Y represents ($C_5$–$C_{15}$)alkyl; ($C_2$–$C_{15}$)olefinic group; ($C_3$–$C_{10}$)monocyclic hydrocarbon group; or phenyl; any of which may be optionally substituted by one or more, same or different substituents selected from the group consisting of the formula $R_5$ defined below; ($C_1$–$C_4$)alkyl substituted by one or more substituents selected for the group $R_5$; or a group of the formula —(Z—O)$_n$—Z, wherein Z is a ($C_1$–$C_3$) alkyl, n is an integer >1; and no continuous linear sequence of atoms in the group Y exceeds 15; $R_5$ represents halogen, hydroxy, mercapto, trifluoromethyl, amino, ($C_1$–$C_3$)alkoxy, ($C_1$–$C_3$)alkylthio, ($C_1$–$C_6$)alkylamino, ($C_1$–$C_3$) alkoxycarbonyl, cyano, azido, nitro, —COOH, —$CONH_2$, —CONHR', or COONR'R' wherein R' represents ($C_1$–$C_3$) alkyl; or a pharmaceutically acceptable salt thereof, or a hydrate or solvate thereof. The compounds are valuable in the human and veterinary therapy.

(I)

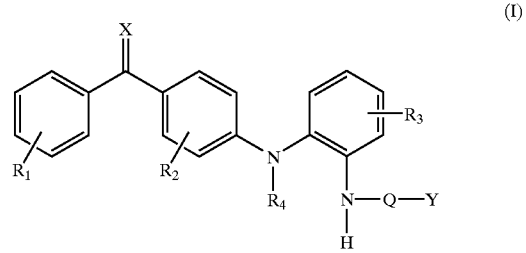

9 Claims, No Drawings

AMINOBENZOPHENONES AS INHIBITORS OF IL-1β AND TNF-α

This application is the national phase under 35 U.S.C. §371 of PCT International Application No. PCT/DK00/00385 which has an International filing date of Jul. 11, 2000, which designated the United States of America and was published in English, which claims benefit of Ser. No. 60/144,166, filed Jul. 16, 1999.

FIELD OF THE INVENTION

This invention relates to a hitherto unknown class of compounds which shows anti-inflammatory effects, to pharmaceutical preparations containing these compounds, to dosage units of such preparations, and to their use in the treatment and prophylaxis of asthma, allergy, arthritis, including rheumatoid arthritis and spondyloarthritis, gout, atherosclerosis, chronic inflammatory bowel disease (Crohn's disease), proliferative and inflammatory skin disorders, such as psoriasis and atopic dermatitis, uveitis, septic shock, AIDS, and acne.

BACKGROUND OF THE INVENTION

Previously, a series of closely related aminobenzophenones (e.g. 4-(2-amino-4-nitro-phenylamino) benzophenone) have been described (Hussein, F. A. et al, Iraqi J. Sci., 22, 54–66 (1981)). However, there is no description of their uses. PCT/DK98/00008 discloses aminobenzophenone inhibitors of interleukin 1β (IL-1β) and tumour necrosis factor a (TNF-α) secretion in vitro, said compounds being potentially useful for treatment of inflammatory diseases in which the production of cytokines is involved in the pathogenesis, e.g. asthma, rheumatoid arthritis, psoriasis, contact dermatitis, and atopic dermatitis. Furthermore the compounds of PCT/DK98/00008 was tested in vivo for anti-inflammatory properties in the 12-O-tetradecanoylphorbol-13-acetate (TPA) induced murine chronic skin inflammation model, (De Young, L. M. et al, Agents Actions, 26, 335–341 (1989); Carlson, R. P. et al, Agents Actions, 17, 197–204 (1985); Alford, J. G. et al, Agents Action, 37, (1992); Stanley, P. L. et al, Skin Pharmacol, 4, 262–271 (1991)). In this chronic skin inflammation model the compounds had the same potency compared to the reference compound hydrocortisone.

The purpose of the present invention is to provide further pharmacologically active aminobenzophenone derivatives and related compounds.

This purpose is achieved with the novel aminobenzophenone derivatives according to the general formula I that are found to be potent inhibitors of interleukin 1β (IL-1β) and tumour necrosis factor α (TNF-α) secretion in vitro, making them potentially useful for treatment of inflammatory diseases, in which the secretion and regulation of cytokines or more specifically interleukin 1β (IL-1β) and tumour necrosis factor α (TNF-α) are involved in the pathogenesis. The inhibition or down regulation of the cytokines is possibly due to an inhibition of MAP kinases.

SUMMARY OF THE INVENTION

The compounds of the present invention are represented by the general formula I below

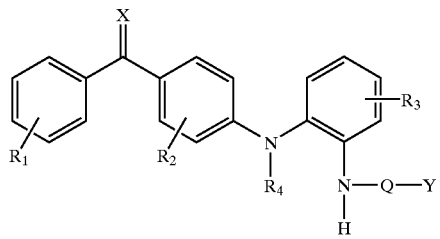

wherein
$R_1$, $R_2$, and $R_3$ represents one or more, same or different substituents selected from the group consisting of halogen, hydroxy, mercapto, trifluoromethyl, amino, $(C_1-C_3)$alkyl, $(C_2-C_3)$olefinic group, $(C_1-C_3)$alkoxy, $(C_1-C_3)$alkylthio, $(C_1-C_6)$alkylamino, $(C_1-C_3)$alkoxycarbonyl, cyano, —$CONH_2$, phenyl, or nitro; further $R_2$ can be hydrogen, and $R_3$ can be carboxy and carbamoyl;

$R_4$ represents hydrogen, $(C_1-C_3)$alkyl, or allyl;

X represents oxygen or sulphur;

Q represents —(CO)—, —(CS)—, or a bond;

Y represents $(C_5-C_{15})$alkyl; $(C_2-C_{15})$olefinic group; $(C_3-C_{10})$monocyclic hydrocarbon group; or phenyl; any of which may be optionally substituted by one or more, same or different substituents selected from the group consisting of the formula $R_5$ defined below; $(C_1-C_4)$alkyl substituted by one or more substituents selected from the group $R_5$; or a group of the formula —(Z—O)$_n$—Z, wherein Z is a $(C_1-C_3)$alkyl, n is an integer >1; and no continuous linear sequence of atoms in the group Y exceeds 15;

$R_5$ represents halogen, hydroxy, mercapto, trifluoromethyl, amino, $(C_1-C_3)$alkoxy, $(C_1-C_3)$alkylthio, $(C_1-C_6)$alkylamino, $(C_1-C_3)$alkoxycarbonyl, cyano, azido, nitro, —COOH, —$CONH_2$, —CONHR', or —COONR'R' wherein R' represents $(C_1-C_3)$alkyl;

or a salt thereof with a pharmaceutically acceptable acid, a hydrate or a solvate thereof.

In compounds of formula I $R_1$ preferably represents one or more, same or different substituents selected from the group consisting of fluoro, chloro, bromo, hydroxy, trifluoromethyl, amino, $(C_1-C_2)$alkyl, $(C_2-C_3)$alkenyl, $(C_1-C_3)$alkoxy, $(C_1-C_3)$alkoxycarbonyl, cyano, or —$CONH_2$;

$R_2$ represents one or more, same or different substituents selected from the group consisting of hydrogen, fluoro, chloro, bromo, hydroxy, trifluoromethyl, amino, $(C_1-C_3)$alkyl, $(C_2-C_3)$alkenyl, $(C_1-C_3)$alkoxy.

$R_3$ represents one or more, same or different substituents selected from the group consisting of hydrogen, halogen, hydroxy, trifluoromethyl, $(C_1-C_3)$alkyl, $(C_2-C_3)$alkenyl, $(C_1-C_3)$alkoxy, $(C_1-C_3)$alkoxycarbonyl, cyano, carboxy, or —$CONH_2$.

$R_4$ represents hydrogen, $(C_1-C_2)$alkyl, or allyl;

X represents oxygen or sulphur;

Q represents —(CO)—, or a bond.

Y represents $(C_5-C_{10})$alkyl; $(C_2-C_{10})$alkenyl; $(C_3-C_8)$cycloalkyl; $(C_5-C_8)$cycloalkene group; or phenyl; any of which may be optionally substituted by one or more, same or different substituents selected from the group consisting of the formula $R_5$ defined below; $(C_1-C_4)$alkyl substituted by one or more substituents with the formula $R_5$; or a group of formula —(Z—O)$_n$—Z, wherein Z is a $(C_1-C_3)$alkyl, n is an integer >1; and no continuous linear sequence of atoms in the group Y exceeds 9;

$R_5$ represents halogen, hydroxy, amino, ($C_1$–$C_2$)alkoxy, ($C_1$–$C_4$)alkylamino, ($C_1$–$C_3$)alkoxycarbonyl, cyano, azido, —COOH, —CONH$_2$, —CONHR', or —CONR'R' wherein R' represents ($C_1$–$C_2$)alkyl.

More preferably $R_1$ represents one or more, same or different substituents selected from the group consisting of fluoro, chloro, bromo, hydroxy, methyl, or methoxy; $R_2$ represents one or more, same or different substituents selected from the group consisting of hydrogen, fluoro, chloro, bromo, hydroxy, methyl, or methoxy; $R_3$ represents one or more, same or different substituents selected from the group consisting of hydrogen, fluoro, chloro, bromo, hydroxy, methyl, or methoxy; $R_4$ represents hydrogen; X represents oxygen; Q represents —(CO)—, or bond; Y represents ($C_5$–$C_7$)alkyl; ($C_2$–$C_4$)alkenyl; any of which may be optionally substituted by one or more, same or different substituents selected from the group consisting of the formula $R_5$, ($C_1$–$C_4$)alkyl, substituted by one or more substituents with the formula $R_5$, and a group of formula —CH$_2$—O—CH$_2$—CH$_2$—O—CH$_3$; $R_5$ preferably represents fluoro, chloro, bromo, hydroxy, amino, ($C_1$–$C_2$)alkoxycarbonyl, —COOH, —CONH$_2$, CON(CH$_3$)$_2$.

It is preferred that Q does not represent —(CO)— in compounds of the formula I where Y is —CF$_3$.

The phenyl group of $R_1$ and $R_2$ may optionally be substituted, e.g. with hydroxy; amino; nitro; cyano; halogen, preferably fluoro, chloro, or bromo; methyl; or methoxy.

Specific compounds of formula I are:

N-[2-[3-Chloro-4-(2-methylbenzoyl)-phenylamino] phenyl]-succinamic acid (Compound 101), 2'-[3-Chloro-4-(2-methylbenzoyl)-phenylamino] octananilide (Compound 102), 4-Bromo-2'-[3-chloro-4-(2-methylbenzoyl)-phenylamino]butananilide (Compound 103), Ethyl 2'-[3-chloro-4-(2-methylbenzoyl)-phenylamino] succinanilate (Compound 104), 2-(2-Methoxy-ethoxy)-2'-[3-chloro-4-(2-methylbenzoyl)-phenylamino]acetanilide (Compound 105), N,N-dimethyl-N'-2-[3-chloro-4-(2-methylbenzoyl)-phenylamino]phenylsuccinamide (Compound 106), 2-Hydroxy-2'-[3-chloro-4-(2-methoxybenzoyl)-phenylamino]acetanilide (Compound 107), 2-Hydroxy-2'-[3-chloro-4-(2-methylbenzoyl)-phenylamino]acetanilide (Compound 108), 2-Hydroxy-2'-[3-fluoro-4-(2-methylbenzoyl)-phenylamino]acetanilide (Compound 109), 2-Amino-2'-[3-chloro-4-(2-methylbenzoyl)-phenylamino]acetanilide (Compound 110), Ethyl 2-[2-[3-chloro-4-(2-methylbenzoyl)-phenylamino]anilino]acetate (Compound 111), 2-Chloro-4-[2-(6-hydroxyhexylamino)phenylamino]-2'-methylbenzophenone (Compound 112), 2-Chloro-4-[2-(3-hydroxypropylamino)phenylamino]-2'-methylbenzophenone (Compound 113), 5'-Bromo-2'-[3-chloro-4-(2-methylbenzoyl)-phenylamino]hexananilide (Compound 114), 5'-Bromo-2'-[3-chloro-4-(2-methylbenzoyl)-phenylamino]but-3-eneanilide (Compound 115), 5'-Bromo-2'-[3-chloro-4-(2-methylbenzoyl)-phenylamino]-4-methylpentananilide (Compound 116), 2'-[3-Chloro-4-(2-methylbenzoyl)-phenylamino]-2-methylpentananilide (Compound 117), N-[5-Bromo-2-[3-chloro-4-(4-ethoxy-2-methylbenzoyl)-phenylamino]phenyl]-succinamic acid (Compound 118), N-[5-Bromo-2-[3-ethoxy-4-(2-methylbenzoyl)-phenylamino]phenyl]-succinamic acid (Compound 119), N-[5-Bromo-2-[3-chloro-4-(2,3-dimethylbenzoyl-phenylamino]phenyl]-succinamic acid (Compound 120), N-[5-Bromo-2-[3-chloro-4-(4-n-butyl-2-methylbenzoyl)-phenylamino]phenyl]-succinamic acid (Compound 121), N-[5-Bromo-2-[3-chloro-4-(4-chloro-2-methylbenzoyl)-phenylamino]phenyl]-succinamic acid (Compound 122), N-[5-Bromo-2-[3-fluoro-4-(2-methylbenzoyl)-phenylamino]phenyl]-succinamic acid (Compound 123), N-[5-Bromo-2-[3-chloro-4-(2,4,5-trimethylbenzoyl)-phenylamino]phenyl]-succinamic acid (Compound 124), N-[5-Bromo-2-[3-chloro-4-(4-fluoro-2-methylbenzoyl)-phenylamino]phenyl]-succinamic acid (Compound 125), N-[5-Bromo-2-[3-chloro-4-(2,5-dimethylbenzoyl)-phenylamino]phenyl]-succinamic acid (Compound 126), N-[5-Bromo-2-[3-fluoro-4-(4-methoxy-2-methylbenzoyl)-phenylamino]phenyl]-succinamic acid (Compound 127), N-[5-Bromo-2-[3-chloro-4-(3-chloro-2-methylbenzoyl)-phenylamino]phenyl]-succinamic acid (Compound 128), and salts thereof with pharmaceutically acceptable acids, hydrates and solvates.

Compounds of formula I wherein X=S according to the formula Ia below are also generally preferred

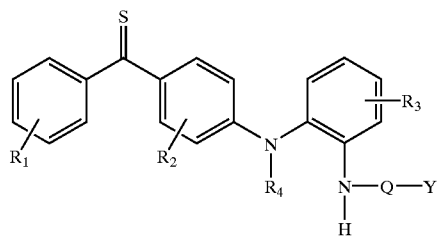

in which $R_1$, $R_2$, $R_3$, $R_4$, Q, and Y have the above meanings.

Specific compounds of formula Ia are:

N-[2-[3-Chloro-4-(2-methyl(thiobenzoyl))-phenylamino] phenyl]-succinamic acid (Compound 129), 2'-[3-Chloro-4-(2-methyl(thiobenzoyl))-phenylamino] octananilide (Compound 130), 4-Bromo-2'-[3-chloro-4-(2-methyl(thiobenzoyl))-phenylamino]butananilide (Compound 131), Ethyl 2'-[3-chloro-4-(2-methyl(thiobenzoyl))-phenylamino]succinanilate (Compound 132), 2-(2-Methoxy-ethoxy)-2'-[3-chloro-4-(2-methyl(thiobenzoyl))-phenylamino]acetanilide (Compound 133), N,N-dimethyl-N'-2-[3-chloro-4-(2-methyl(thiobenzoyl))-phenylamino]phenylsuccinamide (Compound 134), 2-Hydroxy-2'-[3-chloro-4-(2-methoxy(thiobenzoyl))-phenylamino]acetanilide (Compound 135), 2-Hydroxy-2'-[3-chloro-4-(2-methyl(thiobenzoyl))-phenylamino]acetanilide (Compound 136), 2-Hydroxy-2'-[3-fluoro-4-(2-methyl(thiobenzoyl))-phenylamino]acetanilide (Compound 137), 2-Amino-2'-[3-chloro-4-(2-methyl(thiobenzoyl))-phenylamino]acetanilide (Compound 138), Ethyl 2-[2-[3-chloro-4-(2-methyl(thiobenzoyl))-phenylamino]anilino]acetate (Compound 139), 2-Chloro-4-[2-(6-hydroxyhexylamino)phenylaminol]-2'-methyl(thiobenzophenone) (Compound 140), 2-Chloro-4-[2-(3-hydroxypropylamino)phenylamino]-2'-methyl(thiobenzophenone) (Compound 141), 5'-Bromo-2'-[3-chloro-4-(2-methyl(thiobenzoyl))-phenylamino]hexananilide (Compound 142), 5'-Bromo-2'-[3-chloro-4-(2-methyl(thiobenzoyl))-phenylamino]but-3-eneanilide (Compound 143), 5'-Bromo-2'-[3-chloro-4-(2-methyl(thiobenzoyl))-phenylamino]-4-methylpentananilide (Compound 144), 2'-[3-Chloro-4-(2-methyl(thiobenzoyl))-phenylamino]-2-methylpentananilide (Compound 145), N-[5-Bromo-2-[3-chloro-4-(4-ethoxy-2-methyl(thiobenzoyl))-phenylamino]phenyl]-succinamic acid (Compound 146), N-[5-Bromo-2-[3-ethoxy-4-(2-methyl(thiobenzoyl))-phenylamino]phenyl]-succinamic acid (Compound 147), N-[5-Bromo-2-[3-chloro-4-(2,3-dimethyl(thiobenzoyl))-phenylamino]phenyl]-succinamic acid (Compound 148), N-[5-Bromo-2-[3-chloro-4-(4-n-butyl-2-methyl(thiobenzoyl))-phenylamino]phenyl]-succinamic acid (Compound 149), N-[5-Bromo-2-[3-chloro-4-(4-chloro-2-methyl(thiobenzoyl))-phenylamino]phenyl]-succinamic acid (Compound 150), N-[5-Bromo-2-[3-fluoro-4-(2-methyl(thiobenzoyl))-phenylamino]phenyl]-succinamic acid (Compound 151), N-[5-Bromo-2-[3-chloro-4-(2,4,5-trimethyl(thiobenzoyl))-phenylamino]phenyl]-succinamic acid (Compound 152), N-[5-Bromo-2-[3-chloro-4-(4-fluoro-2-methyl(thiobenzoyl))-phenylamino]phenyl]-succinamic acid (Compound 153), N-[5-Bromo-2-[3-chloro-4-(2,5-dimethyl(thiobenzoyl))-phenylamino]phenyl]-succinamic acid (Compound 154), N-[5-Bromo-2-[3-fluoro-4-(4-methoxy-2-methyl(thiobenzoyl))-phenylamino]phenyl]-succinamic acid (Compound 155), N-[5-Bromo-2-[3-chloro-4-(3-chloro-2-methyl(thiobenzoyl))-phenylamino]phenyl]-succinamic acid (Compound156), and salts thereof with pharmaceutically acceptable acids, hydrates and solvates.

Further preferred compounds of general formula I are compounds wherein $R_1$, $R_2$, and $R_3$ represent one substituent. $R_1$ and $R_2$ preferably being in the ortho position.

The compounds of formula I and Ia can be used in the form of their salts which are formed with pharmaceutically acceptable inorganic or organic acids, such as hydrochloric, hydrobromic and hydroiodic acid, phosphoric acid, sulphuric acid, nitric acid, p-toluenesulphonic acid, methanesulphonic acid, formic acid, acetic acid, propionic acid, citric acid, tartaric acid, succinic acid, benzoic acid, maleic acid, these examples being considered as non-limiting for the invention.

As used in the specification, unless specified to the contrary, the following terms have the meaning indicated:

"Alkyl" refers to any univalent groupderived from an alkane by removal of a hydrogen atom from any carbon atom, and includes the subclasses of normal alkyl (n-alkyl), and primary, secondary and tertiary alkyl groups respectively, and having the number of carbon atoms specified, including for example $(C_1-C_3)$alkyl, $(C_1-C_5)$alkyl, $(C_5)$alkyl, $(C_6-C_{10})$alkyl, $(C_6-C_{15})$alkyl, methyl, ethyl, n-propyl, isopropyl, n-butyl, isobutyl, sec-butyl, and t-butyl. Alkane refers to an acyclic branched or unbranched hydrocarbon having the general formula $C_nH_{2n+2}$, and therefore consisting entirely of hydrogen atoms and saturated carbon atoms.

"Olefinic group" refers to a straight or branched acyclic hydrocarbon having one or more carbon-carbon double bonds of either E or Z stereochemistry where applicable, and having the number of carbon atoms specified. The term includes, for example, $(C_2-C_{15})$olefinic group, preferably a $(C_2-C_{15})$alkenyl; $(C_2-C_3)$olefinic group, preferably a $(C_2-C_3)$alkenyl; vinyl; allyl; 1-butenyl; 2-butenyl; and 2-methyl-2-propenyl. Olefinic groups having only one carbon-carbon double bond, herein called alkenyl, are preferred.

"Alkoxy" refers broadly to a radical of the formula —OR, where R is alkyl as defined above, for example $(C_1-C_3)$alkoxy, $(C_1-C_2)$alkoxy, methoxy, ethoxy, n-propoxy, and the like.

"$(C_1-C_3)$alkylthio" refers broadly to a radical of the formula —SR, where R is alkyl as defined above and includes methylthio, ethylthio, n-propylthio, and 2-propylthio.

"$(C_1-C_6)$alkylamino" refers broadly to a radical of the formula —NHR or —NR$_2$, where R is alkyl as defined above having from 1–6 carbon atoms and includes, for example, methylamino, dimethylamino, di-(n-propyl)amino, and n-butyl(ethyl)amino.

"$(C_1-C_3)$alkoxycarbonyl" refers broadly to a radical of the formula —COOR, where R is alkyl as defined above and includes methoxycarbonyl, ethoxycarbonyl, n-propoxycarbonyl, and i-propoxycarbonyl.

"$(C_3-C_{10})$monocyclic hydrocarbon group" includes the saturated cycloalkanes and unsaturated cyclic olefins, such as cycloalkenes having one endocyctic double bond, and having from 3–10 carbon atoms, and includes, for example, $(C_3-C_8)$cycloalkyl, cyclopropyl, cyclopentyl, cyclohexyl, and cyclooctyl, $(C_3-C_{10})$cycloalkene group, and $(C_3-C_8)$ cycloalkene group. Specific examples are cycloprop-2-enyl, cyclobut-2-enyl, cyclopent-2-enyl, cyclohex-3-enyl, and cyclonon-4-enyl.

"Amino" means the group —NH$_2$.

Carbamoyl" refers to any one of the groups —CONH$_2$, —CONHR, and —CONRR' where R and R' represent alkyl as defined above.

"Carboxy" refers to a radical of the formula —COOH.

"Halogen" means the same or different of fluoro, chloro, bromo, and iodo; fluoro, chloro, and bromo being preferred.

Pharmacological Methods

To study the effect of the compound of the present invention in vitro the inhibition of the IL-1β and TNF-α secretion was measured using the following procedure:

Cytokine production was measured in the media from lipopolysaccharide (LPS) stimulated peripheral blood mononuclear cells. The mononuclear cells were isolated from human peripheral blood by Lymphoprep® (Nycomed, Norway) fractionation and suspended in RPMI 1640 (growth medium) with foetal calv serum (FCS, 2%), at a concentration of $5 \times 10^5$ cells/ml. The cells were incubated in 24-well tissue culture plates in 1 ml aliquots. Test compounds were dissolved in dimethylsulfoxide (DMSO, 10 mM) and were diluted with the medium. Compounds were added to the cells for 30 minutes, then LPS (1 mg/ml final concentration) was added. The plates were incubated for 18 hours, and the concentration of IL-1β and TNF-α in the medium was determined by enzyme-linked immunosorbent assays. The median inhibitory concentrations ($IC_{50}$) of the compounds were calculated. The results are shown in Table 1 below.

The compounds of the present invention also show similar activities in the ability to inhibit PMN (polymorphonuclear) superoxide secretion which is also indicative of potentially useful anti-inflammatory drugs. The compounds were tested using the following procedure. Human polymorphonuclear (PMN) granulocytes were isolated from human blood by dextran sedimentation, Lymphoprep® fractionation, and hypotonic lysis of contaminating erythrocytes. Superoxide anion generation was measured as the superoxide dismutase inhabitable reduction of ferricytochrome C (Madhu, S. B. et al, Inflammation, 16, 241, (1992)). The cells were suspended in Hank's balanced salt solution, and incubated for 10 minutes at 37° C. with test compounds. The cells were primed by the addition of TNF-α (3 ng/ml final concentration) for 10 minutes, and then ferricytochrome C, (final concentration 750 μg/ml), bovine serum albumin (BSA, final concentration 1 mg/ml) and formyl-methionyl-leucyl-phenylalanine (fMLP, final concentration $10^{-7}$ M) were added for 3 minutes. The cells were chilled on ice, and were spun down. The optical densities in the cell-free supernatant was measured in a spectrophotometer. The median inhibitory concentration ($IC_{50}$) of the compounds was calculated. The results are shown in Table 1.

TABLE 1

Inhibition of cytokines and PMN-superoxide production in vitro by compounds of the present invention.

| Comp. No.; | IL-1β | TNF-α | PMN-superoxide |
|---|---|---|---|
| | The median inhibition concentration ($IC_{50}$, nM) of | | |
| 101 | 200 | 25 | 63 |
| 102 | 6.3 | 6.3 | 5.0 |
| ref. a) | 13 | 7.1 | 5.0 | ref. a): 4-(2-Aminophenylamino)-2-chloro-2'-methylbenzophenone, compound 106 disclosed in PCT/DK98/00008.

These results show that the compounds of the present invention are able to inhibit the production of IL-1β, TNF-α and PMN-superoxide, and showing a pharmacological activity comparable to a reference compound, thus making them potentially useful in the treatment of inflammatory diseases.

To study the compounds of the present invention in vivo the 12-O-tetradecanoylphorbol-13-acetate (TPA) induced murine chronic skin inflammation model can be used (De Young, L. M. et al, Agents Actions, 26, 335–341 (1989); Carlson, R. P. et al, Agents Actions, 17, 197–204 (1985); Alford, J. G. et al, Agents Action, 37, (1992); Stanley, P. L. et al, Skin Pharmacol, 4, 262–271 (1991)), cf. description of method in PCT/DK98/00008 hereby incorporated by reference. These results show that the compounds of the present invention are of the same potency compared to known reference compounds, e.g. hydrocortisone with its known side effects, whereas the compounds of the present invention are well tolerated and are non-toxic. Some members of the present class of compounds show a very low absorption, thus making them especially useful in the treatment of various dermatological diseases. In general, they may be administered by e.g. oral, intravenous, intranasal, topically or transdermal routes.

Method of Preparation

The compounds of the present invention can be prepared in a number of ways well known to those skilled in the art of organic synthesis. The compounds of the present invention can be synthesised using the methods outlined below, together with methods known in the art of synthetic organic chemistry, or variations thereof as appreciated by those skilled in the art. Preferred methods include, but are not limited to, those described below.

The novel compounds of formula I and Ia may be prepared using the reactions and techniques described in this section. The reactions are performed in solvents appropriate to the reagents and materials employed and are suitable for the transformations being effected. Also, in the synthetic methods described below, it is to be understood that all proposed reaction conditions, including choice of solvent, reaction atmosphere, reaction temperature, duration of experiment and work-up procedures, are chosen to be conditions of standard for that reaction, which should be readily recognised by one skilled in the art. It is understood by one skilled in the art of organic synthesis that the functionality present on various portions of the educt molecule must be compatible with the reagents and reactions proposed. Not all compounds of formula I falling into a given class may be compatible with some of the reaction conditions required in some of the methods described. Such restrictions to the substituents which are compatible with the reaction conditions will be readily apparent to one skilled in the art and alternate methods can be used.

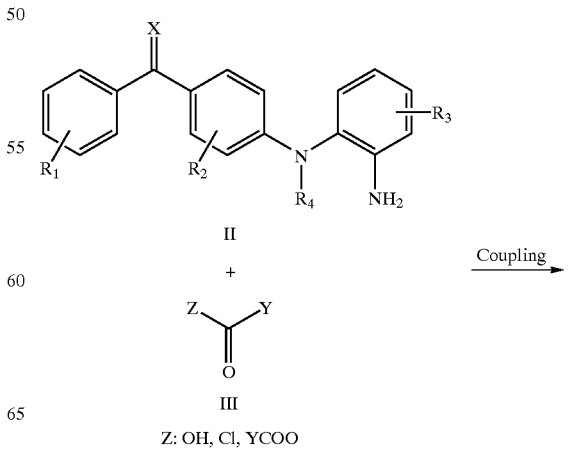

-continued

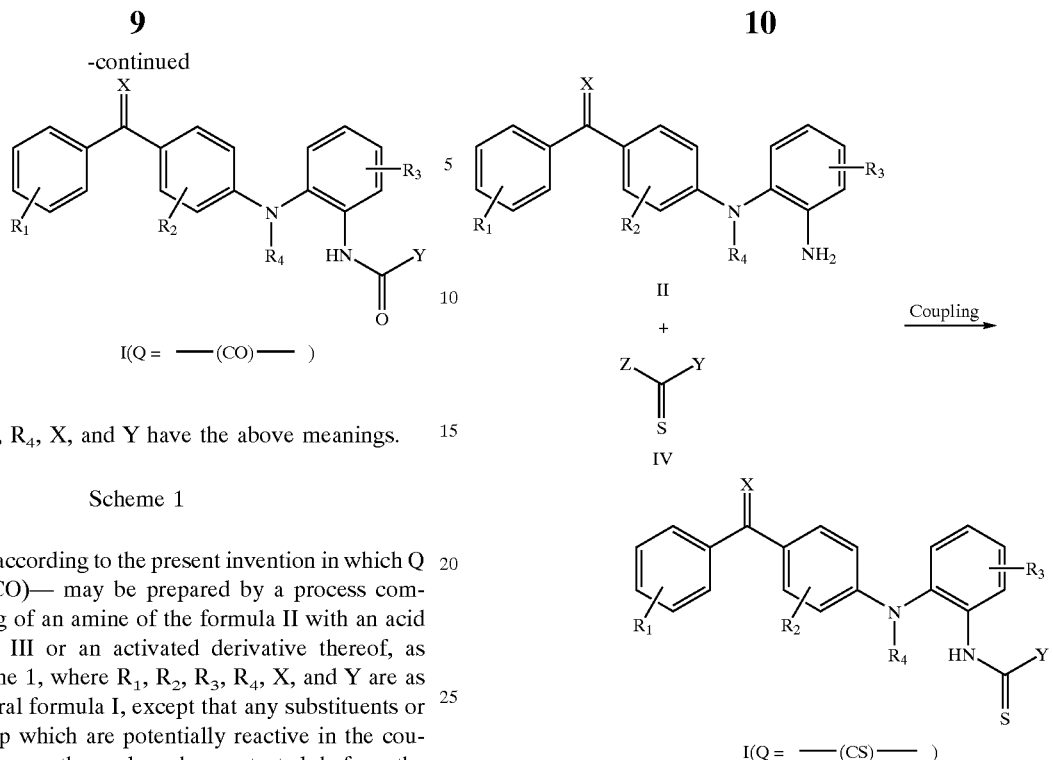

I(Q = —(CO)—)

and $R_1$, $R_2$, $R_3$, $R_4$, X, and Y have the above meanings.

Scheme 1

Compounds according to the present invention in which Q represents —(CO)— may be prepared by a process comprising coupling of an amine of the formula II with an acid of the formula III or an activated derivative thereof, as shown in scheme 1, where $R_1$, $R_2$, $R_3$, $R_4$, X, and Y are as defined in general formula I, except that any substituents or functional group which are potentially reactive in the coupling reaction may themselves be protected before the coupling reaction is performed and subsequently removed.

The coupling reaction or condensation is carried out using any of the many methods for the formation of amide bonds known to one skilled in the art of organic synthesis. These methods include, but are not limited to, the use of standard coupling procedures such as mixed carbonic anhydride (isobutyl chloroformate) method, carbodiimide (N,N-dimethylaminopropyl-N′-ethyl carbodiimide (EDC), dicyclohexyl carbodiimide, diisopropyl carbodiimide) method, active ester (pentafluorophenyl ester, p-nitrophenyl ester, N-hydroxysuccinic imido ester) method, cabonyidiimidazole method, azide method, phosphorous reagents such as BOP-Cl, azide method, conversion of an acid of formula III to an acid chloride. Some of these methods (especially carbodiimide) can be enhanced by the addition of 1-hydroxybenzotriazole (HOBt).

Compounds according to the present invention in which C=X and Q simultaneusly represents —(CS)— may be prepared from compounds of the invention in which C=X or Q, or both represents —(CO)— by a process using an appropiate thiocarbonylating agent such as phosphorous pentasulfide ($P_4S_{10}$), or Lawesson's reagent (2,4-bis(4-methoxyphenyl)-1,3,2,4-dithiaphosphetane-2,4-disulfide) or the like. Alternatively, compounds according to the present invention in which Q represents —(CS)— may be prepared by a process comprising coupling of an amine of the formula II with a thioacylating agent of the formula IV, as shown in scheme 2, where $R_1$, $R_2$, $R_3$, $R_4$, X, and Y are as defined in general formula I, except that any substituents or functional group which are potentially reactive in the coupling reaction may themselves be protected before the coupling reaction is performed and subsequently removed. Examples of such thioacylating agents are, but are not limited too, thionoesters, dithioesters and N-thioacylazoles (derived from imidazole, triazole, benzimidazole and benzotriazole).

and $R_1$, $R_2$, $R_3$, $R_4$, X, and Y have the above meanings.

Scheme 2

Compounds according to the present invention in which Q represents a bond may be prepared by a process comprising coupling of an amine of the formula II with an alkylating agent of the formula V, as shown in scheme 3, where $R_1$, $R_2$, $R_3$, $R_4$, X, and Y are as defined in general formula I, except that any substituents or functional group which are potentially reactive in the coupling reaction may themselves be protected before the coupling reaction is performed and subsequently removed.

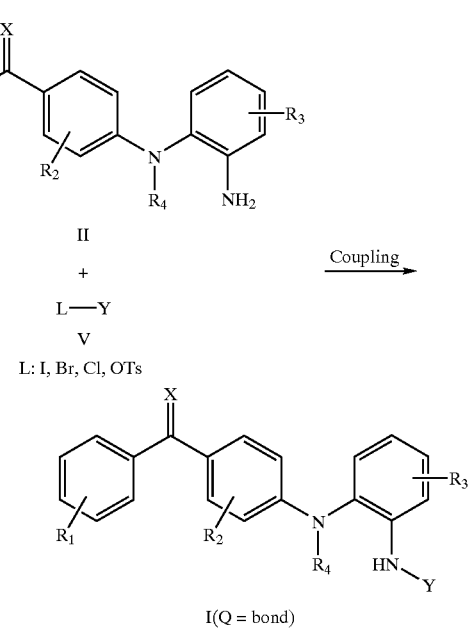

and $R_1$, $R_2$, $R_3$, $R_4$, X, and Y have the above meanings.

Scheme 3

Typically alkylating agents of the general formula V include, but are not limited to, iodides(L=I), bromides(L=Br), chlorides(L=Cl) and sulfonates(L=OSO$_2$R, where R represents methyl, trifluoromethyl or 4-methylphenyl).

Compounds accordingly to the present invention with the general formula II(X=O) may be prepared by several methods known to those skilled in the art of organic synthesis. One useful sequence is shown in scheme 4 were the key process comprising coupling of an amine of the formula VII with an fluoride, chloride, bromide, iodide, or triflate with the formula VIII, as shown in Scheme 4, where $R_1$, $R_2$, $R_3$, and, $R_4$ are as defined in general formula I, to give a coupled product with the general formula VI, except that any substituents or functional group which are potentially reactive in the coupling reaction may themselves be protected before the coupling reaction is performed and subsequently removed. This compound VI may then be reduced to the corresponding amine with the general formula II by treatment with standard reducing agents. Examples of such reducing agents include, but are not limited to, stannous chloride dihydrate; hydrogen, ammonium a formiate, or hydrazine hydrate and a catalytic amount of palladium on carbon.

is the nucleophilc aromatic substiution method which comprising coupling of an amine with an arylfluoride or aryichloride in the presence of a base, in an suitable solvent. Especially potassium-tert-butoxide (KOt-Bu), sodium-tert-butoxide (NaOt-Bu), sodium hydrid (NaH), and potassium hydride (KH) have proven to be the best bases in this process, but other bases may be used as well.

The reaction is typically performed at ambient temperature (20–25° C.) in dipolar aprotic solvents like dimethylsulfoxide (DMSO), dimethylformamide (DMF), or N-methylpyrrolidone (NMP) under an inert atmosphere like argon or nitrogen.

Alternatively, the coupling reaction can be done by the palladium catalysed amination method which comprising coupling of an amine with an arylhalogenide (iodide, bromide, triflate, or in some cases chloride) in the presence of a base, a suitable Pd source, and a suitable phosphine ligand in an inert solvent.

The palladium compound used in the process is not particularly limited, and as specific examples are palladium (II)acetate, palladium(II)chloride, palladium(II)bromide, dichlorobis(triphenylphosphine)palladium(II), tetrakis(triphenylphosphine)palladium(0), tris(dibenzylideneacetone)dipalladium(0). The preferred ligand include, but are not limited to, racemic or non-racemic

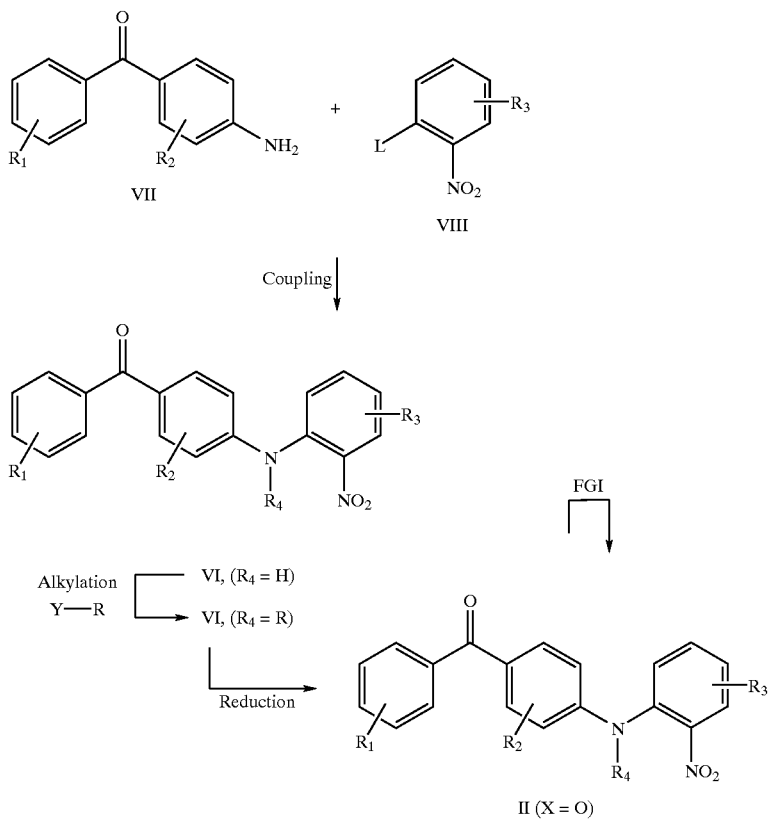

L: Br, I, OSO$_2$CF$_3$, or F and Cl
Y: Cl, Br, OSO$_2$CF$_3$, OSO$_2$CH$_3$, or OTs
FGI: Functional group interconversion and $R_1$, $R_2$, $R_3$, $R_4$, and Y have the above meanings.

Scheme 4

The coupling reaction is carried out using any of the methods for the formation of diphenylamines known to one skilled in the art of organic synthesis. The preferred method 2,2'-bis(diphenylphosphino)-1,1'-binaphthyl (hereinafter referred to as BINAP), tri-o-tolylphosphine, tri-tert-butylphosphine, 1,1'-bis(diphenylphosphino)-ferrocene, bis[(2-diphenylphosphino)phenyl]ether (DPEphos), 2-dicyclohexylphosphanyl-2'-dimethylaminobiphenyl, 2-(di-tert-butylphosphino)biphenyl, and 9,9-dimethyl-4,6-bis(diphenylphosphino)xanthene (Xantphos). The amount of palladium and ligand used in this process is typically in the range 0.1 to 10% by mole relative to the amount of the aromatic halide (or triflate) used. Especially sodium-tert-butoxide (NaOt-Bu) and caesium carbonate ($Cs_2CO_3$) have proven to be the best bases in this process, but other bases may be used as well. The reaction is typically performed at elevated temperature (80–120° C.) in inert solvents like 1,4-dioxane, toluene, benzene and tetrahydrofurane under an inert atmosphere like argon or nitrogen.

Compounds according to the present invention in which $R_4$ is not hydrogen may be prepared by a process comprising coupling of an amine of the formula VI ($R_4$=H) with an alkylating agent, as shown in scheme 4, where $R_1$, $R_2$, $R_3$, and, $R_4$ are as defined in general formula I, except that any substituents or functional group which are potentially reactive in the coupling reaction may themselves be protected before the coupling reaction is performed and subsequently removed.

Typically alkylating agents of the general formula R-Y include, but are not limited to, iodides (Y=I), bromides (Y=Br), chlorides (Y=Cl) and sulfonates (Y=$OSO_2R'$, where R' represents methyl, trifluoromethyl or 4-methylphenyl).

Compounds according to the present invention may in special cases be prepared by a simple functional group interconversion (FGI), meaning a standard process, known to those skilled in the art of organic synthesis, where a functional group in compounds with the general formula I (or any other intermediate described herein) is transformed into a different functional group in one or more synthetic steps, leading to a new compound with the general formula I. Examples of such processes are, but are not limited to, hydrolysis of an ester to give an acid under basic conditions; deprotection of an methylether to give an phenol by treatment with e.g. borontribromide ($BBr_3$); and catalytic hydrogenation of an olefin to give an saturated hydrocarbon.

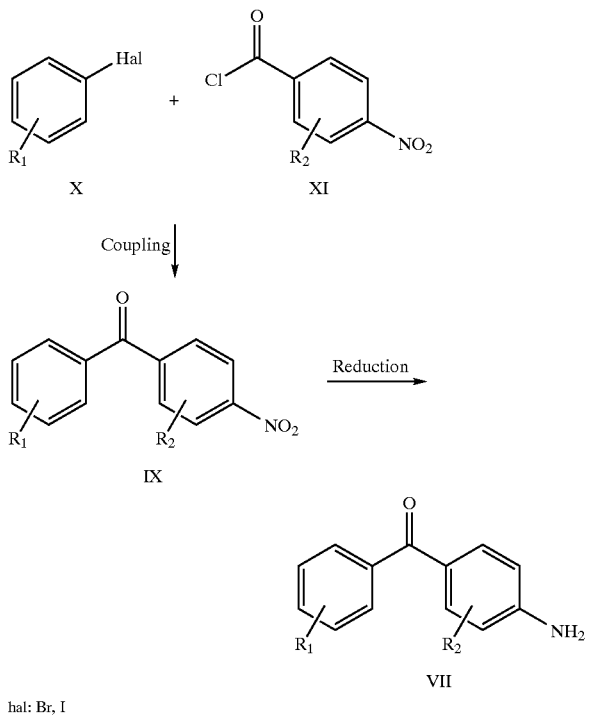

hal: Br, I and $R_1$ and $R_2$ have the above meanings.

Scheme 5

Compounds accordingly to the present invention with the general formula VII may be prepared by several methods known to those skilled in the art of organic synthesis. One useful sequence is shown in Scheme 5. The key step comprises coupling of a bromide (or iodide) with the general formula X with an acid chloride with the general formula XI to afford the benzophenone with the general formula IX. This compound IX may then be reduced to the corresponding amine with the general formula VII by treatment with standard reducing agents. Examples of such reducing agents include, but are not limited to, stannous chloride dihydrate; hydrogen, ammonium formiate, or hydrazine hydrate and a catalytic amount of palladium on carbon. The coupling reaction is done by transforming the bromide (X) into a reactive organometallic intermediate, e.g. by treatment with butyllithium to afford the lithium derivative or by treatment with magnesium to afford the magnesium derivative. The reactivity of this intermediate is then modulated by transmetallation to e.g. zinc, by treatment with $ZnCl_2$, $ZnBr_2$, or $ZnI_2$. This organozinc compound is then coupled with the acid chloride, with the general formula XI, under the influence of a palladium(0) complex in catalytic amount. Examples of such catalyst include but are not particularly limited to tetrakis(triphenylphosphine)palladium(0), tetrakis (triphenylarsine)-palladium(0), dichlorobis (triphenylphosphine)palladium(II), or benzylchlorobis (triphenylphosphine)palladium(II).

It may be more advantageous in some cases to alter the sequence of the processes described above. The described sequence of processes is not considered as being limited for the preparation of the compounds of the present invention with the general formula I and alteration of the reaction sequence is an obvious alternative for those skilled in the art of organic synthesis.

The present compounds are intended for use in pharmaceutical compositions which are useful in the treatment of the above mentioned diseases.

The amount required of a compound of formula I and Ia (hereinafter referred to as the active ingredient) for therapeutic effect will, of course, vary both with the particular compound, the route of administration and the mammal under treatment. A suitable dose of a compound of formula I for systemic treatment is 0.1 to 200 mg/kg bodyweight, the most preferred dosage being 0.2 to 50 mg/kg of mammal bodyweight, administered one or more times daily.

While it is possible for an active ingredient to be administered alone as the raw chemical, it is preferable to present it as a pharmaceutical formulation. Conveniently, the active ingredient comprises from 0.1% to 100% by weight of the formulation. Conveniently, dosage units of a formulation contain between 0.07 mg and 1 g of the active ingredient. For topical administration, the active ingredient preferably comprises from 1% to 20% by weight of the formulation but the active ingredient may comprise as much as 50% w/w.

Formulations suitable for nasal or buccal administration may comprise 0.1% to 20% w/w. for example about 2% w/w of active ingredient.

By the term "dosage unit" is meant a unitary, i.e. a single dose which is capable of being administered to a patient, and which may be readily handled and packed, remaining as a physically and chemically stable unit dose comprising either the active material as such or a mixture of it with solid or liquid pharmaceutical diluents or carriers.

The formulations, both for veterinary and human medical use, of the present invention comprise an active ingredient in association with a pharmaceutically acceptable carrier therefore and optionally other therapeutic ingredient(s). The carrier(s) must be "acceptable" in the sense of being compatible with the other ingredients of the formulations and not deleterious to the recipient thereof.

The formulations include those in a form suitable for oral, ophthalmic, rectal, parenteral (including subcutaneous, intramuscular and intravenous), transdermal, intra-articular, topical, nasal, or buccal administration.

The formulations may conveniently be presented in dosage unit form and may be prepared by any of the methods well known in the art of pharmacy. All methods include the step of bringing the active ingredient into association with the carrier which constitutes one or more accessory ingredients. In general, the formulations are prepared by uniformly and intimately bringing the active ingredient into association with a liquid carrier or a finely divided solid carrier or both, and then, if necessary, shaping the product into the desired formulation.

Formulations of the present invention suitable for oral administration may be in the form of discrete units as capsules, sachets, tablets or lozenges, each containing a predetermined amount of the active ingredient; in the form of a powder or granules; in the form of a solution or a suspension in an aqueous liquid or non-aqueous liquid; or in the form of an oil-in-water emulsion or a water-in-oil emulsion. The active ingredient may also be administered in the form of a bolus, electuary or paste.

Formulations for rectal administration may be in the form of a suppository incorporating the active ingredient and a carrier such as cocoa butter, or in the form of an enema.

Formulations suitable for parenteral administration conveniently comprise a sterile oily or aqueous preparation of the active ingredient which is preferably isotonic with the blood of the recipient.

Formulations suitable for intra-articular administration may be in the form of a sterile aqueous preparation of the active ingredient which may be in microcrystalline form, for example, in the form of an aqueous microcrystalline suspension. Liposomal formulations or biodegradable polymer systems may also be used to present the active ingredient for both intra articular and ophthalmic administration.

Formulations suitable for topical administration, including eye treatment, include liquid or semi-liquid preparations such as liniments, lotions, gels, applicants, oil-in-water or water-in-oil emulsions such as creams, ointments or pastes; or solutions or suspensions such as drops.

Formulations suitable for administration to the nose or buccal cavity include powder, self-propelling and spray formulations, such as aerosols and atomizers.

In addition to the aforementioned ingredients, the formulations of this invention may include one or more additional ingredients.

The compositions may further contain other therapeutically active compounds usually applied in the treatment of the above mentioned pathological conditions, for instance glucocorticoids, vitamin D's, anti-histamines, platelet activating factor (PAF) antagonists, anticolinergic agents, methyl xanthines, β-adrenergic agents, salicylates, indomethacin, flufenamate, naproxen, timegadine, gold salts, penicillamine, serum cholesterol-reducing agents, retinoids, zinc salts, and salicylazosulfapyridin (Salazopyrin).

The novel compounds of the invention are of value in the human and veterinary practice as systemic and topical therapeutic agents for the treatment and prevention of diseases. The novel compounds show anti-acne properties and, i.a., anti-inflammatory and cytokine regulating effects possibly due to MAP kinase inhibition, and are useful in the treatment and prophylaxis of asthma, allergy, arthritis, including rheumatoid arthritis and spondylo-arthritis, gout, atherosclerosis, chronic inflammatory bowel disease (Crohn's disease), proliferative and inflammatory skin disorders, such as psoriasis, atopic dermatitis, uveitis, septic shock, AIDS, and osteoporosis.

The invention will now be further described in the following non-limiting general procedures, preparations and examples.

EXAMPLES

General Procedures, Preparations and Examples

Specific examples of compounds of formula I are listed in Table 2.

All melting points are uncorrected. For $^1$H and $^{13}$C nuclear magnetic resonance (NMR) spectra (300 MHz) chemical shift values (δ) (in ppm) are quoted, unless otherwise specified, for deuteriochloroform and hexadeuterodimethylsulfoxide solutions relative to internal tetramethylsilane (δ 0.00) or chloroform ($^1$H NMR δ 7.25, $^{13}$C NMR δ 76.81). The value for a multiplet (m), either defined (doublet (d), triplet (t), quartet (q)) or not at the approximate mid point is given unless a range is quoted (s singlet, b broad). The organic solvents used were anhydrous. The term "chromatography" refers to column chromatography using the flash technique and was performed on silica gel.

The following abbreviations have been used throughout this specification: $CDCl_3$=deuteriochloroform, DMF=N,N-dimethylformamide, $DMSO-d_6$=hexadeuterodimethylsulfoxide, $Et_3N$=triethylamine, EtOAc=ethyl acetate, $Et_2O$=diethylether, HMPA=hexamethylphosphorous triamide, NMM=N-methylmorpholine, THF=tetrahydrofurane, BOP-Cl=bis(2-oxo-3-oxazolidinyl)phosphinic chloride, TLC=thin layer chromatography.

TABLE 2

Compounds of General formula I

| Comp. No. Example No. | X | $R_1$ | $R_2$ | $R_3$ | $R_4$ | Q | Y |
|---|---|---|---|---|---|---|---|
| 101, Ex. 1 | O | 2-Me | 2-Cl | H | H | —(CO)— | —$(CH_2)_2COOH$ |
| 102, Ex. 2 | O | 2-Me | 2-Cl | H | H | —(CO)— | —$(CH_2)_6CH_3$ |
| 103, Ex. 3 | O | 2-Me | 2-Cl | H | H | —(CO)— | —$(CH_2)_3Br$ |
| 104, Ex. 4 | O | 2-Me | 2-Cl | H | H | —(CO)— | —$(CH_2)_2COOCH_2CH_3$ |
| 105, Ex. 5 | O | 2-Me | 2-Cl | H | H | —(CO)— | —$(CH_2)$—O—$(CH_2)_2$—O—$CH_3$ |

TABLE 2-continued

Compounds of General formula I

| Comp. No. Example No. | X | R1 | R2 | R3 | R4 | Q | Y |
|---|---|---|---|---|---|---|---|
| 106, Ex. 6 | O | 2-Me | 2-Cl | H | H | —(CO)— | —(CH$_2$)$_2$CON(CH$_3$)$_2$ |
| 107, Ex. 7 | O | 2-OMe | 2-Cl | H | H | —(CO)— | —CH$_2$OH |
| 108, Ex. 8 | O | 2-Me | 2-Cl | H | H | —(CO)— | —CH$_2$OH |
| 109, Ex. 9 | O | 2-Me | 2-F | H | H | —(CO)— | —CH$_2$OH |
| 110, Ex. 10 | O | 2-Me | 2-Cl | H | H | —(CO)— | —CH$_2$NH$_2$ |
| 111, Ex. 11 | O | 2-Me | 2-Cl | H | H | Bond | —CH$_2$COOCH$_2$CH$_3$ |
| 112, Ex. 12 | O | 2-Me | 2-Cl | H | H | Bond | —(CH$_2$)$_6$OH |
| 113, Ex. 13 | O | 2-Me | 2-Cl | H | H | Bond | —(CH$_2$)$_3$OH |
| 114, Ex. 14 | O | 2-Me | 2-Cl | 4-Br | H | —(CO)— | —(CH$_2$)$_4$CH$_3$ |
| 115, Ex. 15 | O | 2-Me | 2-Cl | 4-Br | H | —(CO)— | —CH$_2$CH═CH$_2$ |
| 116, Ex. 16 | O | 2-Me | 2-Cl | 4-Br | H | —(CO)— | —(CH$_2$)$_2$CH(CH$_3$)$_2$ |
| 117, Ex. 17 | O | 2-Me | 2-Cl | H | H | —(CO)— | —CH(CH$_3$)(CH$_2$)$_2$CH$_3$ |
| 118, Ex. 18 | O | 2-Me, 4-OEt | 2-Cl | 4-Br | H | —(CO)— | —(CH$_2$)$_2$COOH |
| 119, Ex. 19 | O | 2-Me | 2-OEt | 4-Br | H | —(CO)— | —(CH$_2$)$_2$COOH |
| 120, Ex. 20 | O | 2-Me, 3-Me | 2-Cl | 4-Br | H | —(CO)— | —(CH$_2$)$_2$COOH |
| 121, Ex. 21 | O | 2-Me, 4-(CH$_2$)$_3$CH$_3$ | 2-Cl | 4-Br | H | —(CO)— | —(CH$_2$)$_2$CCOH |
| 122, Ex. 22 | O | 2-Me, 4-Cl | 2-Cl | 4-Br | H | —(CO)— | —(CH$_2$)$_2$COOH |
| 123, Ex. 23 | O | 2-Me | 2-F | 4-Br | H | —(CO)— | —(CH$_2$)$_2$COOH |
| 124, Ex. 24 | O | 2-Me, 4-Me, 5-Me | 2-Cl | 4-Br | H | —(CO)— | —(CH$_2$)$_2$COOH |
| 125, Ex. 25 | O | 2-Me, 4-F | 2-Cl | 4-Br | H | —(CO)— | —(CH$_2$)$_2$COOH |
| 126, Ex. 26 | O | 2-Me, 5-Me | 2-Cl | 4-Br | H | —(CO)— | —(CH$_2$)$_2$COOH |
| 127, Ex. 27 | O | 2-Me, 4-OMe | 2-F | 4-Br | H | —(CO)— | —(CH$_2$)$_2$COOH |
| 128, Ex. 28 | O | 2-Me, 3-Cl | 2-Cl | 4-Br | H | —(CO)— | —(CH$_2$)$_2$COOH |

The numbering in Table 2 refers to the numbering in the formula below

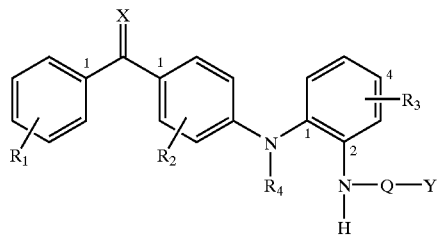

General Procedure 1

Coupling of compounds of the general formula II with compounds of the general formula III (Z=Cl) to give compounds of the general formula (I, Q=O), or a protected derivative thereof.

To a cooled (0° C.) solution of an amine (0.9 mmol), with the general formula II, and Et$_3$N (2.7 mmol) in CH$_2$Cl$_2$ (5 ml) was slowly added a solution of an acid chloride (1.2 mmol), with the general formula III, in CH$_2$Cl$_2$ (1 ml). The mixture was stirred at 0° C. for 2 h and at RT overnight. The reaction mixture was added more CH$_2$Cl$_2$, and the solution was washed succesively with 2 M HCl, water, and brine, then dried (Na$_2$SO$_4$), filtered and concentrated in vacuo. The residue was purified either by crystallization or chromatography to afford the anilide with the general formula I, or a protected derivative thereof.

General Procedure 2

Coupling of compounds of the general formula II with compounds of the general formula III (Z=OH) to give compounds of the general formula I (Q=O), or a protected derivative thereof.

NMM (2.8 mmol) was added to a solution of the acid (2.8 mmol), with the general formula III (Z=O), in THF (10 ml) at −15° C., followed by dropwise addition of isobutyl chloroformate (2.8 mmol). The mixture was stirred for 30 min, the amine (2.0 mmol) in THF (10 ml), with the general formula II, was added, and the resulting slurry was stirred at 0° C. for 1 h and at RT overnight. The reaction mixture was poured into EtOAc, and the solution was washed succesively with 1 M HCl, 25% NaHCO$_3$, and brine, then dried (MgSO$_4$), filtered and concentrated in vacuo. The residue was purified either by crystallization or chromatography to afford the anilide, with the general formula I, or a protected derivative thereof.

General Procedure 3

Alkylation of compounds of the general formula II with compounds of the general formula V to give compounds of the general formula I (Q═bond), or a protected derivative thereof.

To a slurry of an amine (1.0 mmol), with the general formula II, K$_2$CO$_3$ (2.0 mmol), and KI (0.1 mmol) in DMF (5 ml) was added an alkylating agent (1.0 mmol), with the general formula V. The mixture was stirred for 24 h at 25° C., or until the starting material had disappeared, as seen on TLC. The reaction mixture was poured into water (100 ml) and extracted with EtOAc (3*50 ml). The combined organic extracts were whashed with brine, dried (MgSO$_4$), filtered and evaporated in vacuo. The residue was purified by chromatography to afford the alkylated aniline, with the general formula I, or a protected derivative thereof.

General Procedure 4

Coupling of compounds of the general formula II with compounds of the general formula III (Z=YCOO) to give compounds of the general formula (I, Q=O), or a protected derivative thereof.

To a solution of an amine (2.9 mmol), with the general formula II, in acetic acid (100%, 8 ml) was slowly added an acid anhydride (3.8 mmol) with the general formula III. The mixture was stirred at RT for 2 h or until no more starting material was seen on TLC. The reaction mixture was added water, and the solution was stirred for 30 minutes and then extracted with EtOAc twice. The organic phases were dried (MgSO$_4$), filtered and concentrated in vacuo. The residue was purified either by crystallization or chromatography to afford the anilide with the general formula I, or a protected derivative thereof.

Example 1

N-[2-[3-Chloro-4-(2-methylbenzoyl)-phenylamino] phenyl]-succinamic Acid (Compound 101)

A stirred solution of 4-(2-aminophenylamino)-2-chloro-2'-methylbenzophenone (3.0 mmol) in glacial acetic acid (5.0 ml) was heated to 70° C., then succinic anhydride (4.0 mmol) was added. The temperature was held at 100° C. for 20 min after which the reaction mixture was concentrated in vacuo to afford a light brown syrupy, which crystallised on standing. Trituration with a mixture of Et$_2$O/CH$_2$Cl$_2$ 3:1 followed by filtration and washing yielded the product as white crystals.

$^{13}$C NMR (DMSO-d$_6$): δ 195.3, 173.9, 170.6, 149.3, 142.4, 139.4, 136.5, 133.5, 132.4, 131.8, 131.1, 130.7, 128.8, 126.5, 125.7, 125.3, 125.1, 124.5, 123.7, 115.3, 112.2, 30.8, 29.1, 19.8.

Example 2

2'-[3-Chloro-4-(2-methylbenzoyl)-phenylamino] octananilide (Compound 102)

General Procedure: 1
  Starting compound II: 4-(2-Aminophenylamino)-2-chloro-2'-methylbenzophenone
  Starting compound III: Octanoyl chloride
  Purification: Chromatography using EtOAc/pentane 1:3 as eluant
  $^{13}$C NMR (CDCl$_3$): δ 196.8, 172.8, 148.9, 139.2, 137.6, 135.1, 133.7, 132.8, 131.8, 131.2, 130.8, 129.5, 128.3, 126.2, 125.6, 125.4, 124.8, 124.1, 116.0, 112.4, 37.2, 31.6, 29.1, 29.0, 25.7, 22.6, 20.3, 14.0.

Example 3

4-Bromo-2'-[3-chloro-4-(2-methylbenzoyl)-phenylamino]butananilide (Compound 103)

General Procedure: 1
  Starting compound II: 4-(2-Aminophenylamino)-2-chloro-2'-methylbenzophenone
  Starting compound III: 4-Bromobutyryl chloride
  Purification: Chromatography using CH$_2$Cl$_2$ followed by EtOAc/CH$_2$Cl$_2$ 1:20 as eluant
  $^{13}$C NMR (CDCl$_3$): δ 196.8, 171.1, 148.8, 139.1, 137.8, 135.1, 33.6, 132.5, 131.8, 131.3, 130.9, 129.6, 128.7, 126.3, 125.9, 125.4, 125.0, 123.8, 116.1, 112.5, 44.3, 33.8, 27.9, 20.4.

Example 4

Ethyl 2'-[3-chloro-4-(2-methylbenzoyl)-phenylamino]succinanilate (Compound 104)

General Procedure: 2
  Starting compound II: 4-(2-Aminophenylamino)-2-chloro-2'-methylbenzophenone
  Starting compound III: Mono ethyl succinate
  Purification: Chromatography using EtOAc/pentane 1:4 and 1:2 as eluant
  $^{13}$C NMR (CDCl$_3$): δ 196.5, 173.4, 171.0, 148.5, 139.2, 137.9, 35.0, 133.5, 133.4, 131.3, 130.8, 129.6, 128.9, 126.5, 125.4, 125.2, 124.7, 123.8, 116.5, 112.6, 61.2, 29.7, 20.4, 14.2, 14.2.

Example 5

2-(2-Methoxy-ethoxy)-2'-[3-chloro-4-(2-methylbenzoyl)-phenylamino]acetanilide (Compound 105)

General Procedure: 2
  Starting compound II: 4-(2-Aminophenylamino)-2-chloro-2'-methylbenzophenone
  Starting compound III: 2-(2-Methoxyethoxy)acetic acid
  Purification: Chromatography using EtOAc/pentane 1:5 as eluant
  $^{13}$C NMR (CDCl$_3$): δ 196.4, 169.1, 148.7, 139.3, 137.7, 135.0, 33.6, 133.1, 131.2, 130.8, 130.8, 129.5, 128.6, 126.5, 125.4, 125.3, 124.5, 124.0, 116.2, 112.5, 71.5, 71.3, 70.5, 59.1, 20.4.

Example 6

N,N-dimethyl-N'-2-[3-chloro-4-(2-methylbenzoyl)-phenylamino]phenylsuccinamide (Compound 106)

General Procedure: 2
  Starting compound II: 4-(2-Aminophenylamino)-2-chloro-2'-methylbenzophenone
  Starting compound III: N,N-Dimethylsuccinamic acid
  Purification: Chromatography using EtOAc as eluant
  $^{13}$C NMR (CDCl$_3$): δ 196.5, 172.2, 148.5, 139.4, 137.8, 134.9, 133.7, 133.5, 131.2, 130.7, 130.3, 129.6, 128.5, 126.2, 125.3, 125.3, 124.4, 122.5, 116.7, 112.5, 37.1, 35.8, 32.4, 29.6, 20.4.

Example 7

2-Hydroxy-2'-[3-chloro-4-(2-methoxybenzoyl)-phenylamino]acetanilide (Compound 107)

General Procedure: 1
  Starting compound II: 4-(2-Aminophenylamino)-2-chloro-2'-methoxybenzophenone
  Starting compound III: Acetoxyacetyl chloride
  Purification of the O-acetylated derivative (I) was done by chromatography using Et$_2$O/pentane 1:4 as eluant. Deprotection: The protected derivative (I) (0.38 mmol) and K$_2$CO$_3$ (0.5 mmol) was stirred in MeOH (5 ml) for 1 h at ambient temperature. The reaction mixture was poured into EtOAc, and the solution was washed successively with water and brine, then dried (Na$_2$SO$_4$), filtered and concentrated in vacuo to afford a weakly coloured solid product.
  Mp: 180.0–181.3° C.; $^{13}$C NMR (DMSO-d$_6$): δ 192.3, 170.5, 157.1, 149.7, 133.7, 133.4, 132.8, 132.4, 130.6, 129.4, 129.2, 126.8, 125.7, 125.4, 124.8, 122.2, 120.4, 114.7, 112.0, 111.7, 61.5, 55.6.

Example 8

2-Hydroxy-2'-[3-chloro-4-(2-methylbenzoyl)-phenylamino]acetanilide (Compound 108)

By following the procedure of example 7, but substituting 4-(2-aminophenylamino)-2-chloro-2'-methylbenzophenone for 4-(2-aminophenylamino)-2-chloro-2'-methoxybenzophenone, the desired compound was obtained. The compound was further purified by chromatography using EtOAc/pentane 1:1 as eluant.

Mp: 127–129° C.; $^{13}$C NMR (CDCl$_3$): δ 197.4, 170.9, 149.0, 138.8, 138.0, 135.0, 133.5, 132.1, 131.4, 131.4, 131.2, 129.9, 128.6, 126.4, 126.2, 125.4, 125.3, 123.4, 116.1, 112.4, 62.4, 20.5.

Example 9

2-Hydroxy-2'-[3-fluoro-4-(2-methylbenzoyl)-phenylamino]acetanilide (Compound 109)

By following the procedure of example 7, but substituting 4-(2-aminophenylamino)-2-fluoro-2'-methylbenzophenone for 4-(2-aminophenylamino)-2-chloro-2'-methoxybenzophenone, the desired compound was obtained. The compound was further purified by crystallization from $CH_2Cl_2$.

Mp: 149–150° C.; $^{13}$C NMR (DMSO-$d_6$): δ 192.8, 170.5, 164.6, 161.2, 152.6, 152.4, 140.5, 134.9, 133.4, 132.9, 130.5, 130.3, 129.8, 127.3, 126.0, 125.7, 125.4, 124.8, 122.3, 115.7, 115.5, 109.8, 100.0, 99.7, 61.5, 19.2.

Example 10

2-Amino-2'-[3-chloro-4-(2-methylbenzoyl)-phenylamino]acetanilide (Compound 110)

General Procedure: 2

Starting compound II: 4-(2-Aminophenylamino)-2-chloro-2'-methylbenzophenone

Starting compound III: N-(9-Fluorenylmethoxycarbonyl)-glycine

Purification of the FMOC-protected derivative (I) was done by chromatography using EtOAc/pentane 1:4 and 1:2. Deprotection: The protected derivative (I) (0.16 mmol) and CsF (0.33 mmol) was stirred in a mixture of $CH_2Cl_2$ (6 ml) and $CH_3CN$ (2 ml) for 6 days at ambient temperature. The reaction mixture was poured into water and EtOAc and the organic phase was separated. The aqueous phase was extracted with more EtOAc. The organic phases were dried ($MgSO_4$), filtered and concentrated in vacuo to give the crude product which was purified by chromatography using EtOAc/pentane 1:2 as eluant.

$^{13}$C NMR (CDCl$_3$): δ 196.6, 171.8, 148.8, 139.3, 137.7, 135.0, 133.6, 132.6, 131.5, 131.2, 130.8, 129.5, 128.5, 126.2, 125.7, 125.3, 124.8, 123.4, 116.1, 112.4, 44.9, 20.4.

Example 11

Ethyl 2-[2-[3-chloro-4-(2-methylbenzoyl)-phenylamino]anilino]acetate (Compound 111)

General Procedure: 3

Starting compound II: 4-(2-Aminophenylamino)-2-chloro-2'-methylbenzophenone

Starting compound V: Ethyl bromoacetate

Purification: Chromatography using EtOAc/pentane 1:2 as eluant $^{13}$C NMR (CDCl$_3$): δ 196.5, 171.1, 149.9, 143.6, 139.4, 137.7, 135.1, 133.6, 131.2, 130.6, 129.5, 128.2, 127.8, 126.9, 125.8, 125.3, 118.4, 115.6, 112.0, 111.8, 61.4, 45.7, 20.4, 14.2.

Example 12

2-Chloro-4-[2-(6-hydroxyhexylamino)phenylamino]-2'-methylbenzophenone (Compound 112).

To a solution of 4-(2-Aminophenylamino)-2-chloro-2'-methylbenzophenone (0.50 mmol) in HMPA (5 ml) was added 6-bromohexanol (0.76 mmol) and $NaHCO_3$ (5.0 mmol). The mixture was stirred for 24 h at 60° C., more 6-bromohexanol (0.36 mmol) was added and stirring was continued for 6 h. The reaction mixture was poured into ice water and extracted with EtOAc. The combined organic extracts were washed with brine, dried ($MgSO_4$), filtered and concentrated in vacuo. The residue was purified by chromatography twice using EtOAc/hexane 1:2 and then $Et_2O$/hexane 1:4 as eluant to afford the alkylated aniline as an oil.

$^1$H NMR (CDCl$_3$): δ 7.05–7.40 (m, 8H), 6.60–6.80 (m, 3H), 6.53 (dd, 1H), 5.49 (s, 1H), 3.97 (bs, 1H), 3.60 (bt, 2H), 3.13 (bt, 2H), 2,47 (s, 3H), 1.20–1.70 (m, 8H).

Example 13

2-Chloro-4-[2-(3-hydroxypropylamino)phenylamino]-2'-methylbenzophenone (Compound 113)

To a solution of 4-(2-Aminophenylamino)-2-chloro-2'-methylbenzophenone (10.0 mmol) in HMPA (50 ml) was added 3-bromopropanol (25.8 mmol) and $NaHCO_3$ (50 mmol). The mixture was stirred for 72 h at 60–70° C. The reaction mixture was poured into ice water and the precipitated product was filtered off, washed with water and dried. The crude product was purified by chromatography using EtOAc/$Et_2O$ 1:9 as eluant to afford the alkylated aniline as an oil.

$^{13}$C NMR (DMSO-$d_6$): δ 195.0, 151.0, 144.2, 139.6, 136.1, 133.6, 130.9, 130.4, 128.5, 127.0, 126.1, 125.5, 125.2, 124.6, 115.6, 114.3, 111.2, 110.6, 58.6, 39.9, 31.7, 19.6.

Example 14

5'-Bromo-2'-[3-chloro-4-(2-methylbenzoyl)-phenylamino]hexananilide (Compound 114)

General Procedure: 1

Starting compound II: 4-(2-Amino-4-bromophenylamino)-2-chloro-2'-methylbenzophenone Starting compound III: Hexanoyl chloride Purification: Chromatography using EtOAc/pentane 1:4 as eluant $^{13}$C NMR (CDCl$_3$): δ 196.8, 172.5, 148.3, 138.9, 137.9, 135.0, 133.5, 133.5, 131.4, 131.3, 131.1, 129.7, 129.3, 129;0, 126.3, 125.4, 118.5, 116.2, 112.7, 37.3, 31.3, 25.2, 22.4, 20.5, 13.9.

Example 15

5'-Bromo-2'-[3-chloro-4-(2-methylbenzoyl)-phenylamino]but-3-eneanilide (Compound 115)

General Procedure: 2

Starting compound II: 4-(2-Amino-4-bromophenylamino)-2-chloro-2'-methylbenzophenone Starting compound III: 3-Butenoic acid Purification: Chromatography using dichloromethane as eluant $^{13}$C NMR (CDCl$_3$): δ 196.9, 169.8, 148.4, 138.8, 137.8, 135.0, 133.5, 131.4, 131.1, 130.8, 130.3, 129.7, 129.1, 128.9, 126.4, 125.9, 125.4, 120.8, 118.7, 116.2, 112.6, 42.1, 20.4.

Example 16

5'-Bromo-2'-[3-chloro-4-(2-methylbenzoyl)-phenylamino]-4-methylpentananilide (Compound 116)

General Procedure: 1

Starting compound II: 4-(2-Amino-4-bromophenylamino)-2-chloro-2'-methylbenzophenone Starting compound III: 4-methyl pentanoyl chloride Purification: Chromatography using EtOAc/pentane 1:6 as eluant $^{13}$C NMR (CDCl$_3$): δ 196.7, 172.7, 148.3, 138.9, 138.0, 135.0, 133.5, 133.4, 131.4, 131.3, 131.1, 129.7, 129.4, 129.0, 126.3, 125.4, 118.5, 116.3, 112.7, 35.3, 34.3, 27.7, 22.3, 20.5.

Example 17

2'-[3-Chloro-4-(2-methylbenzoyl)-phenylamino]-2-methylpentananilide (Compound 117)

General Procedure: 1

Starting compound II: 4-(2-Aminophenylamino)-2-chloro-2'-methylbenzophenone

Starting compound III: 2-Methyl pentanoyl chloride

Purification: Chromatography using EtOc/pentane 1:4 as eluant $^{13}$C NMR (CDCl$_3$): δ 196.6, 176.0, 148.9, 139.2, 137.8, 135.1, 133.6, 132.6, 132.1, 131.3, 130.8, 129.6, 128.8, 126.3, 126.1, 125.4, 123.8, 115.8, 112.3, 42.0, 36.6, 20.6, 20.4, 17.9, 14.0.

Example 18

N-[5-Bromo-2-[3-chloro-4-(4-ethoxy-2-methylbenzoyl)-phenylamino]phenyl]-succinamic acid (Compound 118)

By following the procedure of example 1, but substituting 4-(2-Amino-4-bromophenylamino)-2-chloro-4'-ethoxy-2'-methylbenzophenone for 4-(2-aminophenylamino)-2-chloro-2'-methylbenzophenone, the desired compound was obtained.

$^{13}$C NMR (CDCl$_3$): δ 198.3, 179.0, 170.9, 162.2, 146.7, 142.8, 135.0, 134.5, 133.1, 131.0, 130.1, 130.0, 129.8, 129.5, 128.3, 121.7, 118.0, 116.6, 114.9, 113.7, 111.1, 63.7, 30.4, 29.1, 21.9, 14.7.

Example 19

N-[5-Bromo-2-[3-ethoxy-4-(2-methylbenzoyl)-phenylamino]phenyl]-succinamic acid (Compound 119)

By following the procedure of example 1, but substituting 4-(2-Amino-4-bromophenylamino)-2-ethoxy-2'-methylbenzophenone for 4-(2-aminophenylamino)-2-chloro-2'-methylbenzophenone, the desired compound was obtained. The compound was further purified by crystallization from mixtures of dichloromethane and n-hexane.

$^{13}$C NMR ( ): δ 195.3, 173.7, 170.8, 160.0, 150.1, 142.9, 134.3, 132.6, 132.2, 132.1, 129.9, 128.7, 127.5, 126.8, 126.5, 125.0, 124.5, 118.6, 114.7, 107.2, 98.1, 62.9, 30.7, 28.8, 19.2, 13.5.

Example 20

N-[5-Bromo-2-[3-chloro-4-(2,3-dimethylbenzoyl)-phenylamino]phenyl]-succinamic acid (Compound 120)

By following the procedure of example 1, but substituting 4-(2-Amino-4-bromophenylamino)-2-chloro-2',3'-dimethylbenzophenone for 4-(2-aminophenylamino)-2-chloro-2'-methylbenzophenone, the desired compound was obtained. The compound was further purified by crystallization from mixtures of dichloromethane and n-hexane.

$^{13}$C NMR ( ): δ 195.6, 173.7, 170.7, 148.9, 140.3, 137.4, 134.2, 133.8, 133.6, 133.3, 131.6, 131.2, 127.5, 126.7, 126.6, 125.7, 125.3, 125.1, 115.7, 112.1, 30.7, 28.8, 19.6, 16.0.

Example 21

N-[5-Bromo-2-[3-chloro-4-(4-n-butyl-2-methylbenzoyl)-phenylamino]phenyl]-succinamic acid (Compound 121)

By following the procedure of example 1, but substituting 4-(2-Amino-4-bromophenylamino)-4'-n-butyl-2-chloro-2'-methylbenzophenone for 4-(2-aminophenylamino)-2-chloro-2'-methylbenzophenone, the desired compound was obtained.

$^{13}$C NMR (CDCl$_3$): δ 199.4, 178.9, 170.9, 147.9, 147.0, 139.4, 135.1, 134.4, 133.6, 132.0, 131.9, 131.5, 130.2, 129.5, 128.4, 125.7, 122.0, 116.6, 115.2, 113.6, 35.6, 33.2, 30.4, 29.1, 22.4, 21.2, 13.9.

Example 22

N-(5-Bromo-2-[3-chloro-4-(4-chloro-2-methylbenzoyl)-phenylamino]phenyl]-succinamic acid (Compound 122)

By following the procedure of example 1, but substituting 4-(2-Amino-4-bromophenylamino)-2,4'-dichloro-2'-methylbenzophenone for 4-(2-aminophenylamino)-2-chloro-2'-methylbenzophenone, the desired compound was obtained. The compound was further purified by crystallization from mixtures of dichloromethane and n-hexane.

$^{13}$C NMR (DMSO-d$_6$): δ 194.1, 173.7, 170.7, 148.9, 139.1, 137.9, 135.1, 133.4, 133.3, 131.2, 130.7, 130.5, 127.5, 126.7, 126.4, 125.6, 125.3, 115.8, 115.5, 112.3, 30.7, 28.8, 19.4.

Example 23

N-[5-Bromo-2-(3-fluoro-4-(2-methylbenzoyl)-phenylamino]phenyl]-succinamic acid (Compound 123)

By following the procedure of example 1, but substituting 4-(2-Amino-4-bromophenylamino)-2-fluoro-2'-methylbenzophenone for 4-(2-aminophenylamino)-2-chloro-2'-methylbenzophenone, the desired compound was obtained. The compound was further purified by crystallization from mixtures of dichloromethane and n-hexane.

$^{13}$C NMR (DMSO-d$_6$): δ 192.8, 173.7, 170.8, 162.7, 151.3, 140.5, 134.9, 133.4, 133.1, 131.1, 130.5, 129.8, 127.5, 127.3, 126.7, 125.6, 125.4, 116.0, 115.9, 110.3, 100.6, 30.7, 28.8, 19.2.

Example 24

N-[5-Bromo-2-[3-chloro-4-(2,4,5-trimethylbenzoyl)-phenylamino]phenyl]-succinamic acid (Compound 124)

By following the procedure of example 1, but substituting 4'-(2-Amino-4-bromophenylamino)-2'-chloro-2,4,5-trimethylbenzophenone for 4-(2-aminophenylamino)-2-chloro-2'-methylbenzophenone, the desired compound was obtained. The compound was further purified by crystallization from mixtures of dichloromethane and n-hexane.

$^{13}$C NMR (DMSO-d$_6$): δ 195.2, 173.7, 170.7, 148.2, 139.7, 136.2, 134.3, 133.2, 133.1, 132.8, 132.8, 132.4, 131.5, 130.4, 127.8, 127.5, 126.7, 124.9, 115.5, 115.4, 112.3, 30.7, 28.8, 19.4, 19.2, 18.6.

Example 25

N-[5-Bromo-2-[3-chloro-4-(4-fluoro-2-methylbenzoyl)-phenylamino]phenyl]-succinamic acid (Compound 125)

By following the procedure of example 1, but substituting 4-(2-Amino-4-bromophenylamino)-2-chloro-4'-fluoro-2'-methylbenzophenone for 4-(2-aminophenylamino)-2-chloro-2'-methylbenzophenone, the desired compound was obtained.

$^{13}$C NMR (CDCl$_3$): δ 197.7, 178.6, 170.9, 164.5, 147.6, 142.4, 134.3, 134.0, 133.6, 133.5, 132.0, 130.8, 129.6, 129.1, 128.0, 123.1, 118.6, 116.4, 116.1, 113.5, 112.7, 30.7, 29.1, 21.1.

Example 26

N-[5-Bromo-2-[3-chloro-4-(2,5-dimethylbenzoyl)-phenylamino]phenyl]-succinamic acid (Compound 126)

By following the procedure of example 1, but substituting 4-(2-Amino-4-bromophenylamino)-2-chloro-2',5'-dimethylbenzophenone for 4-(2-aminophenylamino)-2-chloro-2'-methylbenzophenone, the desired compound was obtained. The compound was further purified by crystallization from mixtures of dichloromethane and n-hexane.

$^{13}$C NMR (DMSO-d$_6$): δ 195.3, 173.7, 170.7, 148.6, 139.0, 134.6, 133.3, 133.2, 133.2, 131.3, 130.9, 129.1, 127.5, 127.0, 126.7, 125.1, 115.6, 112.3, 30.7, 28.8, 20.3, 19.3.

Example 27

N-[5-Bromo-2-[3-fluoro-4-(4-methoxy-2-methylbenzoyl)-phenylamino]phenyl]-succinamic acid (Compound 127)

By following the procedure of example 1, but substituting 4-(2-Amino-4-bromophenylamino)-2-fluoro-4'-methoxy-2'-methylbenzophenone for 4-(2-aminophenylamino)-2-chloro-2'-methylbenzophenone, the desired compound was obtained. The compound was further purified by crystallization from mixtures of dichloromethane and n-hexane.

$^{13}$C NMR (DMSO-d$_6$): δ 191.9, 173.7, 170.8, 162.0, 160.7, 150.4, 138.9, 133.2, 132.8, 132.1, 131.4, 131.1, 127.5, 126.7, 125.2, 117.0, 116.3, 115.6, 110.6, 110.4, 100.7, 55.2, 30.7, 28.8, 20.1.

Example 28

N-[5-Bromo-2-[3-chloro-4-(3-chloro-2-methylbenzoyl)-phenylamino]phenyl]-succinamic acid (Compound 128)

By following the procedure of example 1, but substituting 4-(2-Amino-4-bromophenylamino)-2,3'-dichloro-2'-methylbenzophenone for 4-(2-aminophenylamino)-2-chloro-2'-methylbenzophenone, the desired compound was obtained. The compound was further purified by crystallization from mixtures of dichloromethane and n-hexane.

$^{13}$C NMR (DMSO-d$_6$): δ 193.8, 173.7, 170.7, 149.4, 142.2, 134.5, 134.2, 134.0, 133.5, 133.2, 130.9, 130.7, 127.5, 127.2, 126.7, 126.6, 125.6, 125.4, 116.0, 115.7, 112.2, 30.7, 28.8, 16.6.

Example 29

| Tablet containing compound 111 | |
|---|---|
| Compound 111 (active substance) | 50 mg |
| Lactose | 125 mg |
| Starch | 12 mg |
| Methyl cellulose | 2 mg |
| Sodium carboxymethyl cellulose | 10 mg |
| Magnesium stearate | 1 mg |

The active substance, lactose and starch are mixed to a homogeneous state in a suitable mixer and moistened with a 5 per cent aqueous solution of methyl cellulose 15 cps. The mixing is continued until granules are formed. If necessary, the wet granulation is passed through a suitable screen and dried to a water content of less than 1% in a suitable drier, e.g. fluid bed or drying oven. The dried granules are passed through a 1 mm screen and mixed to a homogeneous state with sodium carboxymethyl cellulose. Magnesium stearate is added, and the mixing is continued for a short period of time. Tablets with a weight of 200 mg are produced from the granulation by means of a suitable tabletting machine.

Example 30

Formulation for Injection Containing Compound 111.

| Compound 111 (active substance) | 1% |
|---|---|
| Sodium chloride | q.s. |
| Ethanol | 10% |
| Water for injection to make | 100% |

The active substance is dissolved in ethanol (10%) then water for injection made isotonic with sodium chloride is added to make 100%. The mixture is filled into ampoules and sterilized.

Example 31

Cream Formulation Containing Compound 101

Compound 101 (10 g) was dissolved in Octyldodecyl myristate (250 g) to form Part A. Methylparaben (1 g) and propylparaben (0.2 g) were dissolved in phenoxyethanol (6 g) and mixed with a 0.025 M Phosphate buffer pH=7.5 (632,8 g) to form Part B. Cetostearyl alcohol (50 g) and ARLACEL 165® (50 g) was melted in a vessel at 70° to 80° C. Part A was added and heated to 60–70° C. The aqueous phase was likewise heated to 60–70° C. and slowly added to the melted oil phase under high speed stirring. The homogenized components were cooled to room temperature.

What is claimed is:

1. A compound of the general formula I

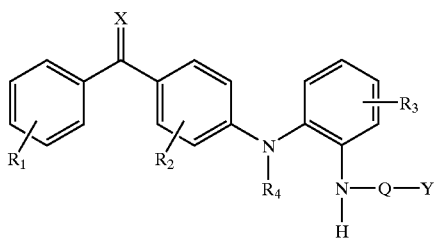

wherein

R$_1$ and R$_3$ represent one or more, same or different substituents selected from the group consisting of halogen, hydroxy, mercapto, trifluoromethyl, amino, (C$_1$–C$_3$)alkyl, (C$_2$–C$_3$)olefinic group, (C$_1$–C$_3$)alkoxy, (C$_1$–C$_3$)alkylthio, (C$_1$–C$_6$)alkylamino, (C$_1$–C$_3$)-alkoxycarbonyl, cyano, —CONH$_2$, phenyl and nitro, provided that when R$_1$ represents one substituent, it is in the ortho position, and when R$_1$ represents more than one substituent, at least one R$_1$ substituent is in the ortho position; R$_2$ represents one substituent in the ortho position, said substituent being selected from the group consisting of hydrogen, halogen, hydroxy, mercapto, trifluoromethyl, amino, (C$_1$–C$_3$)alkyl, (C$_2$–C$_3$) olefinic group, (C$_1$–C$_3$)alkoxy, (C$_1$–C$_3$) alkylthio, (C$_1$–C$_6$)alkylamino, (C$_1$–C$_3$)-alkoxycarbonyl, cyano, —CONH$_2$, phenyl and nitro; and R$_3$ can further be hydrogen, carboxy and carbamoyl;

R$_4$ represents hydrogen, (C$_1$–C$_3$)alkyl, or allyl;

X represents oxygen or sulphur;

Q represents —(CO)—, —(CS)—, or a bond;

Y represents (C$_5$–C$_{15}$)alkyl, except that when Q is a bond, Y is (C$_6$–C$_{15}$)alkyl or (C$_5$–C$_{15}$)alkyl substituted by R$_5$; (C$_2$–C$_{15}$)olefinic group; (C$_3$–C$_{10}$)monocyclic hydrocarbon group; or phenyl; any of which may be optionally substituted by one or more, same or different substituents selected from the group consisting of the formula R$_5$ defined below; (C$_1$–C$_4$)alkyl substituted by one or more substituents selected from the group R$_5$; or a group of the formula —(Z—O)$_n$—Z, wherein Z is a (C$_1$–C$_3$)alkyl, n is an integer >1; and no continuous linear sequence of atoms in the group Y exceeds 15;

R$_5$ represents halogen, hydroxy, mercapto, trifluoromethyl, amino, (C$_1$–C$_3$)alkoxy, (C$_1$–C$_3$) alkylthio, (C$_1$–C$_6$)alkylamino, (C$_1$–C$_3$)alkoxycarbonyl, cyano, azido, nitro, —COOH, —CONH$_2$, —CONHR', or COONR'R' wherein R' represents (C$_1$–C$_3$)alkyl;

or a pharmaceutically acceptable salt thereof, or a hydrate or solvate thereof.

2. A compound according to claim 1 wherein

R$_1$ represents one or more, same or different substituents selected from the group consisting of fluoro, chloro, bromo, hydroxy, trifluoromethyl, amino, (C$_1$–C$_2$)alkyl, (C$_2$–C$_3$)olefinic group, (C$_1$–C$_3$)alkoxy, (C$_1$–C$_3$) alkoxycarbonyl, cyano and CONH$_2$;

R$_2$ represents a substituent selected from the group consisting of hydrogen, fluoro, chloro, bromo, hydroxy, trifluoromethyl, amino, (C$_1$–C$_3$)alkyl, (C$_2$–C$_3$)olefinic group and (C$_1$–C$_3$)alkoxy;

R$_3$ represents one or more, same or different substituents selected from the group consisting of hydrogen, halogen, hydroxy, trifluoromethyl, (C$_1$–C$_3$)alkyl, (C$_2$–C$_3$)olefinic group, (C$_1$–C$_3$)alkoxy, (C$_1$–C$_3$) alkoxycarbonyl, cyano, carboxy and —CONH$_2$;

R$_4$ represents hydrogen, (C$_1$–C$_2$)alkyl or allyl;

X represents oxygen;

Q represents —(CO)—, or a bond;

Y represents (C$_6$–C$_{10}$)alkyl; (C$_2$–C$_{10}$)olefinic group; (C$_3$–C$_8$)cycloalkyl; (C$_3$–C$_8$)cycloalkene group; or phenyl; any of which maybe optionally substituted by one or more, same or different substituents selected from the group consisting of the formula R$_5$ defined below, (C$_1$–C$_5$)alkyl substituted by one or more substituents with the formula R$_5$, and a group of formula —(Z—O)$_n$—Z, wherein Z is a (C$_1$–C$_3$)alkyl, n is an integer >1 wherein no continuous linear sequence of atoms in the group Y exceeds 9;

R$_5$ represents halogen, hydroxy, amino, (C$_1$–C$_2$)alkoxy, (C$_1$–C$_4$)alkylamino, (C$_1$–C$_3$)alkoxycarbonyl, cyano, azido, —COOH, —CONH$_2$, —CONHR', or —CONR'R' wherein R' represents (C$_1$–C$_2$)alkyl.

3. A compound according to claim 1 wherein

R$_1$ represents one or more, same or different substituents selected from the group consisting of fluoro, chloro, bromo, hydroxy, methyl and methoxy;

R$_2$ represents a substituent selected from the group consisting of hydrogen, fluoro, chloro, bromo, hydroxy, methyl and methoxy;

R$_3$ represents one or more, same or different substituents selected from the group consisting of hydrogen, fluoro, chloro, bromo, hydroxy, methyl and methoxy;

R$_4$ represents hydrogen or (C$_1$–C$_2$)alkyl;

Y represents (C$_5$–C$_7$)alkyl; or (C$_2$–C$_4$)alkenyl; any of which may be optionally substituted by one or more, same or different substituents selected from the group consisting of the formula R$_5$; or (C$_1$–C$_4$)alkyl substituted by one or more substituents with the formula R$_5$ representing fluoro, chloro, bromo, hydroxy, amino, (C$_1$–C$_2$)alkoxycarbonyl, —COOH, —CONH$_2$, or CON(CH$_3$)$_2$; and a group of formula —CH$_2$—O—CH$_2$—CH$_2$—O—CH$_3$.

4. A compound according to claim 1 wherein Q does not represent —(CO)— when Y is —CF$_3$.

5. A compound according to claim 1 and selected from the group consisting of

N-[2-[3-Chloro-4-(2-methylbenzoyl)-phenylamino] phenyl]-succinamic acid (Compound 101), 2'-[3-Chloro-4-(2-methylbenzoyl)-phenylamino] octananilide (Compound 102), 4-Bromo-2'-[3-chloro-4-(2-methylbenzoyl)-phenylamino]butananilide (Compound 103), Ethyl 2'-[3-chloro-4-(2-methylbenzoyl)-phenylamino] succinanilate (Compound 104), 2-(2-Methoxy-ethoxy)-2'-[3-chloro-4-(2-methylbenzoyl)-phenylamino]acetanilide (Compound 105), N,N-dimethyl-N'-2-[3-chloro-4-(2-methylbenzoyl)-phenylamino]phenylsuccinamide (Compound 106), 2-Hydroxy-2'-[3-fluoro-4-(2-methylbenzoyl)-phenylamino]acetanilide (Compound 109), 2-Amino-2'-[3-chloro-4-(2-methylbenzoyl)-phenylamino]acetanilide (Compound 110), Ethyl 2-[2-[3-chloro-4-(2-methylbenzoyl)-phenylamino] anilino]acetate (Compound 111), 5'-Bromo-2'-[3-chloro-4-(2-methylbenzoyl)-phenylamino]but-3-eneanilide (Compound 115), 5'-Bromo-2'-[3-chloro-4-(2-methylbenzoyl)-phenylamino]-4-methylpentananilide (Compound 116), N-[5-Bromo-2-[3-ethoxy-4-(2-methylbenzoyl)-phenylamino]phenyl]-succinamic acid (Compound 119), N-[5-Bromo-2-[3-chloro-4-(2,3-dimethylbenzoyl)-phenylamino]phenyl]-succinamic acid (Compound 120), N-[5-Bromo-2-[3-chloro-4-(4-chloro-2-methylbenzoyl)-phenylamino]phenyl]-succinamic acid (Compound 122), N-[5-Bromo-2-[3-fluoro-4-(2-methylbenzoyl)-phenylamino]phenyl]-succinamic acid (Compound 123), N-[5-Bromo-2-[3-chloro-4-(2,4,5-trimethylbenzoyl)-phenylamino]phenyl]-succinamic acid (Compound 124), N-[5-Bromo-2-[3-chloro-4-(2,5-dimethylbenzoyl)-phenylamino]phenyl]-succinamic acid (Compound 126), and salts thereof with pharmaceutically acceptable acids, hydrates and solvates.

6. A compound according to claim 1 and having the general formula Ia

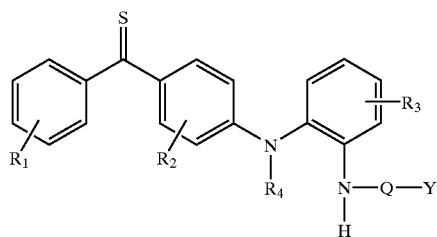

wherein $R_1$, $R_2$, $R_3$, $R_4$, Q, and Y have the meanings specified in claim 1.

7. A compound according to claim 6 and selected from the group consisting of

N-[2-[3-Chloro-4-(2-methy(thiobenzoyl))-phenylamino]phenyl]-succinamic acid (Compound 129), 2'-[3-Chloro-4-(2-methyl(thiobenzoyl))-phenylamino]octananilide (Compound 130), 4-Bromo-2'-[3-chloro-4-(2-methyl(thiobenzoyl))-phenylamino]butananilide (Compound 131), Ethyl 2'-[3-chloro-4-(2-methyl(thiobenzoyl))-phenylamino]succinanilate (Compound 132), 2-(2-Methoxy-ethoxy)-2'-[3-chloro-4-(2-methyl(thiobenzoyl))-phenylamino]acetanilide (Compound 133), N,N-dimethyl-N'-2-[3-chloro-4-(2-methyl(thiobenzoyl))-phenylamino]phenylsuccinamide (Compound 134), 2-Hydroxy-2'-[3-fluoro-4-(2-methyl(thiobenzoyl))-phenylamino]-acetanilide (Compound 137), 2-Amino-2'-[3-chloro-4-(2-methyl(thiobenzoyl))-phenylamino]acetanilide (Compound 138), Ethyl 2-[2-[3-chloro-4-(2-methyl(thiobenzoyl))-phenylamino]anilino]acetate (Compound 139), 5'-Bromo-2'-[3-chloro-4-(2-methyl(thiobenzoyl))-phenylamino]but-3-eneanilide (Compound 143), 5'-Bromo-2'-[3-chloro-4-(2-methyl(thiobenzoyl))-phenylamino]-4-methylpentananilide (Compound 144), N-[5-Bromo-2-[3-ethoxy-4-(2-methyl(thiobenzoyl))-phenylamino]phenyl]-succinamic acid (Compound 147), N-[5-Bromo-2-[3-chloro-4-(2,3-dimethyl(thiobenzoyl))-phenylamino]phenyl]-succinamic acid (Compound 148), N-[5-Bromo-2-[3-chloro-4-(4-chloro-2-methyl(thiobenzoyl))-phenylamino]phenyl]-succinamic acid (Compound 150), N-[5-Bromo-2-[3-fluoro-4-(2-methyl(thiobenzoyl))-phenylamino]phenyl]-succinamic acid (Compound 151), N-[5-Bromo-2-[3-chloro-4-(2,4,5-trimethyl(thiobenzoyl))-phenylamino]phenyl]-succinamic acid (Compound 152), N-[5-Bromo-2-[3-chloro-4-(2,5-dimethyl(thiobenzoyl))-phenylamino]phenyl]-succinamic acid (Compound 154), and salts thereof with pharmaceutically acceptable acids, hydrates and solvates.

8. A pharmaceutical composition containing as an active ingredient a compound according to claim 1 together with a pharmaceutically acceptable carrier and optionally together with a second active ingredient optionally selelcted from the group consisting of glucocorticoids, vitamin D's, anti-histamines, platelet activating factor (PAF) antagonists, anti-colinergic agents, methyl xanthines, β-adrenergic agents, salicylates, indomethacin, flufenamae, naproxen, timegadine, gold salts, penicillamine, serum cholesterol-reducing agents, retinoids, zinc salts, and salicylazosulfapy-ridin (Salazopyrin).

9. A method for the treatment and/or prophylaxis of asthma, allergy, arthritis, including rheumatoid arthritis and spondyloarthritis, gout, atherosclerosis, chronic inflammatory bowel disease (Crohn's disease), proliferative and inflammatory skin disorders, such as psoriasis, atopic dermatitis, uveitis, septic shock, AIDS, and osteoporosis, characterized in administering to patients suffering from said diseases an effective amount of one or more compounds described in claim 1, optionally together or concomitantly with one or more other therapeutically active components selected from the group consisting of glucocorticoids, vitamin D's, anti-histamines, platelet activating factor (PAF) antagonists, anticolinergic agents, methyl xanthines, β-adrenergic agents, salicylates, indomethacin, flufenamate, naproxen, timegadine, gold salts, penicillamine, serum cholesterol-reducing agents, retinoids, zinc salts, and salicylazosulfapyridin (Salazopyrin), and a pharmaecutically acceptable carrier.

* * * * *